United States Patent
Nord

[19]
[11] Patent Number: 5,915,381
[45] Date of Patent: Jun. 29, 1999

[54] BREATHING APPARATUS AND METHOD FOR CONTROLLING SAME

[75] Inventor: Magnus Nord, Bromma, Sweden

[73] Assignee: Siemens Elema AB, Solna, Sweden

[21] Appl. No.: 08/759,302

[22] Filed: Dec. 2, 1996

[30] Foreign Application Priority Data

Dec. 1, 1995 [SE] Sweden ................................. 9504312

[51] Int. Cl.$^6$ ................................................ A61M 16/00
[52] U.S. Cl. .............................. 128/204.23; 128/204.18; 128/204.21; 128/204.26
[58] Field of Search ..................... 128/204.18, 204.21, 128/204.22, 204.23, 204.26, 205.24

[56] References Cited

U.S. PATENT DOCUMENTS

| 4,031,885 | 6/1977 | Davis et al. . | |
| 4,036,221 | 7/1977 | Hillsman et al. | 128/204.23 |
| 4,587,967 | 5/1986 | Chu et al. | 128/205.11 |
| 5,575,283 | 11/1996 | Sjoestrand | 128/204.23 |

FOREIGN PATENT DOCUMENTS

| 0 671 180 | 9/1995 | European Pat. Off. . |
| PS 27 44 327 | 4/1982 | Germany . |

*Primary Examiner*—John G. Weiss
*Assistant Examiner*—Joseph F. Weiss, Jr.
*Attorney, Agent, or Firm*—Hill & Simpson

[57] ABSTRACT

In a method and apparatus for controlling breathing of a patient, momentary compliance is calculated during an inspiration. The calculated momentary compliance is then compared to a threshold value. If momentary compliance is less than the threshold value during a first interval, positive end expiratory pressure is reduced for subsequent breathing cycles so momentary compliance is greater than the threshold value during the first interval. If momentary compliance is less than the threshold value during a second interval, the ratio between inspiration time and expiration time, as well as the breathing rate, is changed so momentary compliance is greater than the threshold value during the second interval, at the same time as a pre-defined minute volume is generated.

16 Claims, 1 Drawing Sheet

BREATHING APPARATUS AND METHOD FOR CONTROLLING SAME

BACKGROUND OF THE INVENTION

1. Field of the Invention

The present invention is directed to a breathing apparatus, such as a ventilator or an anesthetic apparatus, wherein breathing gas is delivered to and removed from a respiratory system at the same time as the pressure and flow of the breathing gas is being measured, at least during delivery of the breathing gas, as well as to a method for controlling such a breathing apparatus.

2. Description of the Prior Art

Breathing apparatus supplying a breathing gas to a respiratory system (in humans or animals) and carrying expired breathing gas out of the respiratory system must be controlled in some way in order to avoid risks of damage to the respiratory system. In particular, the supply operation must be appropriately controlled. Preventing an excessive rise in pressure is essential, since excessive pressure could cause barotrauma. In a corresponding manner, supplying large volumes f gas to the respiratory system could cause volutrauma.

This is particularly the case in the ventilation of patients with diseased or damaged lungs. Ventilators connected to the patient's lungs are generally equipped with, or connected to, flow and pressure meters. Pressure and volume in the lungs can thus be monitored with the aid of pressure and flow measurements.

One problem in monitoring a patient with respect to pressure and volume is that damage-causing levels of pressure and volume can vary from patient to patient. In some patients, damaging pressure builds up in certain parts of the lung, whereas pressure remains on a harmless level in other parts of the lung.

At the same time, pressure must not be allowed to drop too much in certain patients, since their lungs might then collapse, making it necessary to supply an extra large amount of breathing gas to re-open the lungs. Lung collapse can also be partial, i.e. only parts of the lungs collapse. Positive end expiratory pressure (PEEP), a greater than atmospheric pressure produced at the end of expiration, is sued for keeping the lung open until the following inspiration commences.

In addition, the patient must also be supplied with a sufficient amount of breathing gas. Breathing gas supplied can be designated in terms of the minute volume supplied.

SUMMARY OF THE INVENTION

An object of the invention is to provide a method for controlling breathing apparatuses which solves the aforementioned problems.

Another object of the invention is to achieve a breathing apparatus which permits safe and reliable delivery of breathing gas to a respiratory system.

The above object is inventively achieved in a breathing apparatus, and in a method for controlling a breathing apparatus, wherein a breathing gas is delivered to and removed from a respiratory system at the same time as the pressure and flow of the breathing gas are being measured, at least during delivery of the breathing gas, and wherein a momentary compliance of the respiratory system is calculated from the measured pressure and flow at selected points in the inspiratory phase and this compliance is compared to a predetermined threshold value. One or more of the pressure level, PEEP, a ratio between the inspiration time and the expiration time, or the breathing rate is changed if the calculated momentary compliance is less than the predetermined threshold.

Compliance designates the elasticity of the respiratory system. Compliance is determined as the ratio between volume and pressure in the respiratory system. A healthy lung has high compliance and can therefore accommodate relatively large changes in volume without major changes in pressure. Pressure rises rapidly, when there is a small increase in volume, only when the lung's physical volume limitations are approached. In other words, compliance drops rapidly when the healthy lung nears its maximum volume.

The situation is rather different for a damaged or diseased lung. At the start of inspiration with a collapsed lung, pressure rises rapidly with small changes in volume, so compliance is initially very poor. When the lung then opens, compliance is more like the compliance of the healthy lung but is usually much poorer. If the lung is also inherently stiff (atelectatic), the upper limit for volume capacity is reached more quickly, i.e. the stiffness of the lung, rather than the thorax, governs when the lung is full, and compliance drops rapidly. In other words, the damaged or diseased lung has a much smaller effective ventilation range than a healthy lung.

Momentary compliance (the ratio between the derivative of volume and the derivative of pressure in the respiratory system) is therefore an excellent control parameter. When an appropriate threshold value is determined for each patient, parameters such as the level of pressure, PEEP, inspiration time, expiration time, respiratory rate etc. can be automatically controlled by the breathing apparatus.

DESCRIPTION OF THE PREFERRED EMBODIMENTS

Figure 1:
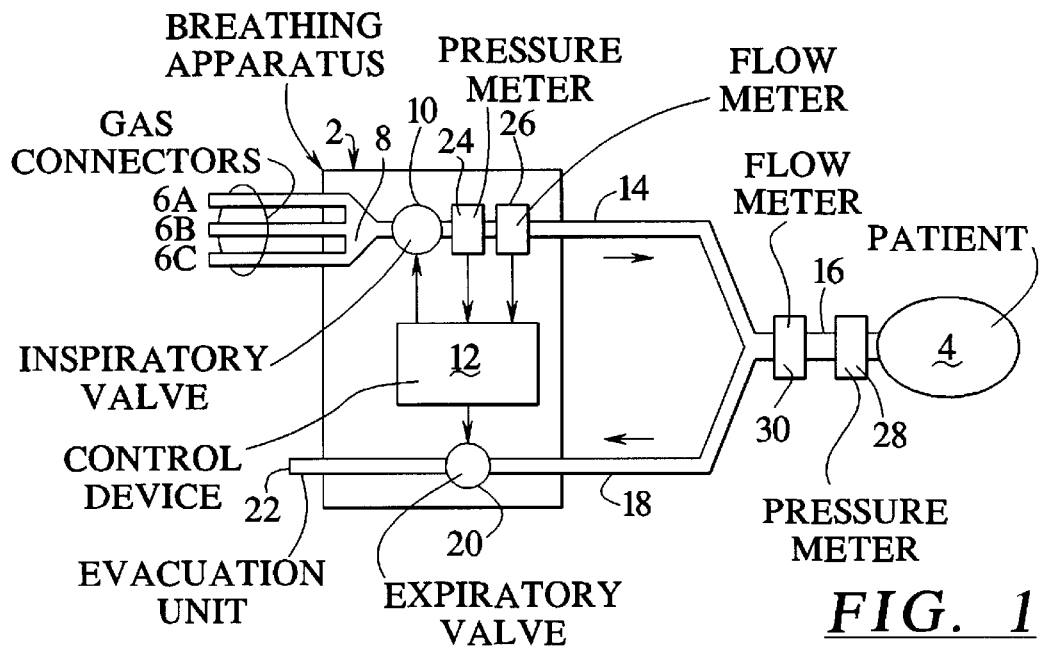
FIG. 1 shows an embodiment of the breathing apparatus according to the invention.

In FIG. 1, a breathing apparatus 2 is connected to a patient 4 to supply the patient 4 with breathing gas and remove expired breathing gas.

The breathing apparatus 2 can accommodate one or a plurality of gases, via three gas connectors (inlets) of 6A, 6B and 6C, which are then mixed into a breathing gas in a mixing chamber 8. Regulation of breathing gas supplied to the patient 4 is performed via an inspiratory valve 10 which is regulated by a control device 12. Alternatively, the respective gas can be regulated at the gas connectors 6A, 6B and 6C, i.e. before the breathing gas is mixed in the mixing chamber 8.

Breathing gas is carried from the breathing apparatus 2 to the patient 4 in an inspiratory line 14 and a connector line 16. The connector line 16 can include a breathing mask or a Y-piece with a tracheal tube or some other known connector means. Expired breathing gas is carried from the patient 4 back to the breathing apparatus 2 through the connector line 16 and an expiratory line 18. An expiratory valve 20 is arranged in the expiratory line 18. The expiratory valve 20 is regulated by the control device 12. With it a positive end expiratory pressure (PEEP) can be maintained at the end of expiration to e.g. prevent collapse of the lung of the patient 4. Expired breathing gas can be discharged into ambient air through an evacuation unit 22 or collected from the evacuation unit 22 for analysis, filtering or similar.

A pressure meter 24 and a flow meter 26 are arranged in the breathing apparatus 2 to measure the pressure and flow of the breathing gas. The measurement signals can be used for regulating the inspiratory valve 10 so the correct pressure and/or flow are/is supplied to the patient 4. With the aid of measurement signals, pressure and flow in or near the lungs of the patient 4 and airways can be calculated. Volume can be determined from flow. Momentary compliance can be determined when pressure and flow are known, as is described in greater detail in connection with FIG. 2. It should be noted that pressure and flow meters can also be arranged near the patient 4, as illustrated with the meters 28 and 30 in FIG. 1. More accurate values for the actual conditions in or near the patient 4 are accordingly obtained. The pressure meter can also be situated in the respiratory system of the patient 4, e.g. near the carina.

Figure 2:
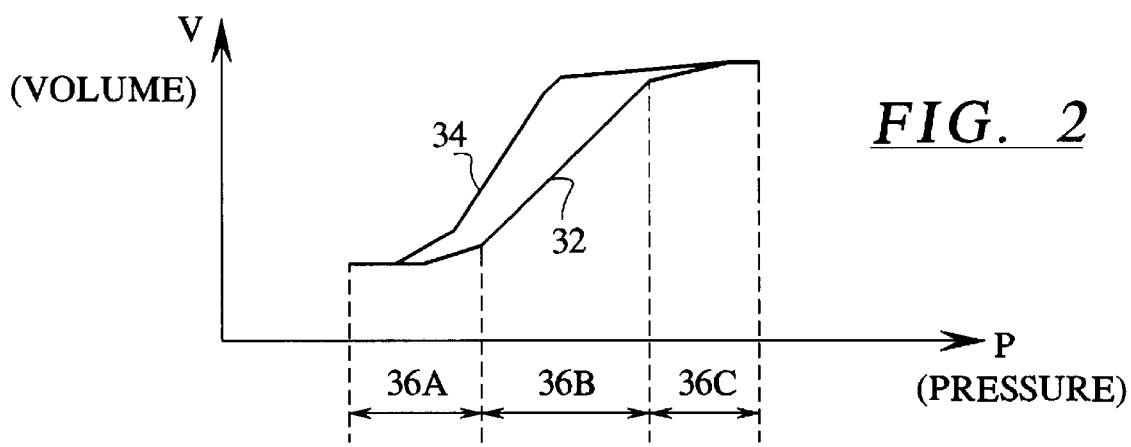
FIG. 2 shows a respiratory curve.

The pressure-volume diagram in FIG. 2 shows an inspiratory and expiratory curve for a diseased or damaged lung. The diagram shows an inspiratory curve 32 and an expiratory curve 34. "Pressure" refers to absolute pressure in the lung, and "volume" refers to the supplied (inspired) volume. As the inspiratory curve 32 shows, pressure initially (area 36A) rises more rapidly than volume. This may be because the lung has collapsed in whole or part and a large positive pressure is needed to open the lung to permit the influx of breathing gas. Compliance in area 36A is accordingly poor.

When the lung has opened (area 36B), breathing gas can flow in more easily, so pressure does not increase as rapidly. This area displays the lung's maximum compliance. The lung ultimately expands as much as it can and is accordingly full. Breathing gas is unable to flow in as easily (area 36C), and every increase in volume causes a sharp rise in pressure. Thus compliance is again poor in the area 36C.

During expiration (curve 34), pressure and volume drop back to their initial values. Since expiration is passive, and the expiratory valve 20 in the breathing apparatus 2 regulates flow and pressure in expiration, the expiratory curve 34 is therefore of less interest than the inspiratory curve 32.

If momentary compliance is determined, the breathing apparatus can be controlled so ventilation only takes place in area 36B in which the lung displays maximum compliance. Here, momentary compliance can be determined in a number of ways. Volume and pressure can be established and the ratio of the respective derivatives can be calculated. Alternatively, the momentary flow value can be divided by the derivative of momentary pressure. Derivatives can be determined in the known manner.

Figure 3:
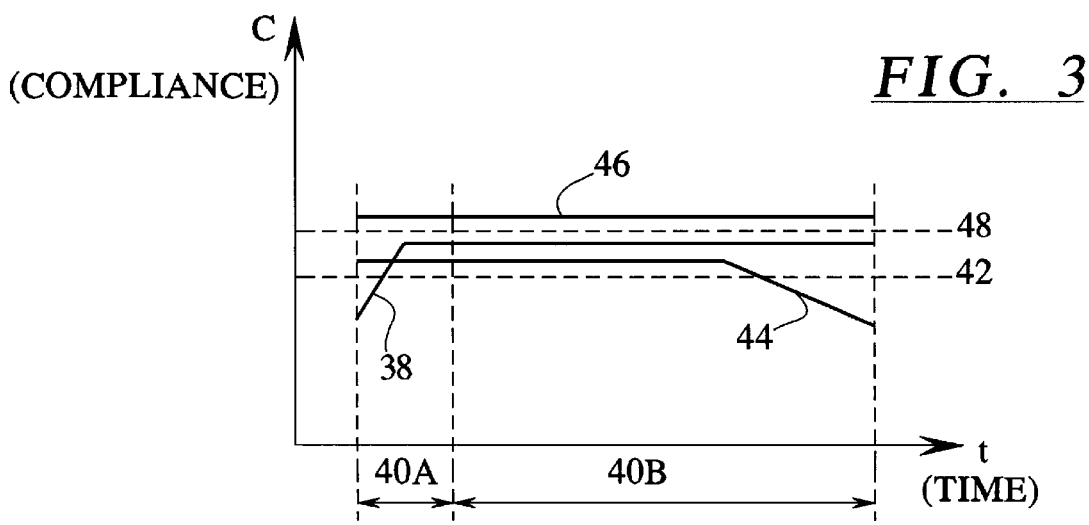
FIG. 3 shows several compliance curves during inspiration.

FIG. 3 shows three of the situations, which can occur during an inspiration, in order to illustrate the invention. The diagram shows compliance on one axis and time on the other. A first compliance curve 38 shows that compliance in a first interval 40A rises sharply and passes a first threshold value 42. Compliance then remains constant for the rest of inspiration, a second interval 40B. The rapidly rising compliance during the first interval 40A indicates that at least some of the lung opens up at the start of inspiration. This imposes a needless pressure load on the lungs, so the PEEP value set is automatically switched to a higher value. The increase can be performed in specific steps until the all of the first compliance curve 38 is above the first threshold value throughout inspiration. Alternatively, a new PEEP can be calculated from measured pressure immediately after compliance exceeds the first threshold value 42.

A second compliance curve 44 is initially constant, but compliance drops below the first threshold value 42 at the end of the second interval 40B. This means that inspiration occurred in the third area 36C in FIG. 2, so excessively high pressure could develop in the lungs. The duration of inspiration is therefore shortened somewhat in order to reduce the risk of harmful excess pressure. A simultaneous change in rate may be necessary to ensure that s sufficient minute volume of breathing gas is supplied to the patient. As an additional safety precaution for some patients, it may be necessary to terminate inspiration as soon as compliance drops below the first threshold value 42. Momentary compliance can also be utilized for determining appropriate reference pressures in pressure-controlled modes, such as PC and PRVC.

The third situation is illustrated by the third compliance curve 46 which is on a constantly high level throughout inspiration. It is even higher than a second threshold value 48. This could mean that the patient's condition has improved and that the first threshold value is no longer relevant. The breathing apparatus can then automatically switch to the use of the second threshold value in the manner described above. Thus, ventilation can be continuously adapted to the patients' condition. If the patient's condition worsens, however, a physician should decide on the course of future treatment.

The high compliance of the third compliance curve 46 also suggests that only part of the maximum area 36B is being utilized in ventilation. PEEP can therefore be successively reduced, in order to reduce peak inspiratory pressure (PIP). At the same time, minute volume can be increased by prolongation of inspiration time. If the minute volume is the target volume, the breathing rate can be reduced at the same time.

Momentary compliance needs not be calculated continuously. From the compliance curves shown, it is apparent that the beginning and end of the inspiration are of greatest interest. It would therefore be sufficient for the operation of the method according to the invention to study these parts only.

The invention has been described above in conjunction with a ventilator. But the same method can be implemented in e.g. anesthetic equipment and other breathing apparatuses. It is also important to avoid the build-up of excessive pressure in healthy lungs, e.g. because more breathing gas is supplied in inspiration than is removed in expiration. Analysis of momentary compliance supplies an additional control parameter for the patient's safety.

Although modifications and changes may be suggested by those skilled in the art, it is the intention of the inventors to embody within the patent warranted hereon all changes and modifications as reasonably and properly come within the scope of their contribution to the art.

I claim as my invention:

1. A breathing apparatus comprising:

means for delivering a breathing gas to and removing expired breathing gas from, a respiratory system;

means for measuring a pressure and a flow of said breathing gas at least during delivery of said breathing gas;

calculating means for calculating a momentary compliance of said respiratory system from respective measurements of said pressure and flow obtained at selected points in time during delivery of said breathing gas in an inspiratory phase;

means for comparing said momentary compliance to a threshold value; and adjustment means for, if said momentary compliance is less than said threshold value, changing at least one parameter in a group of parameters consisting of pressure level, PEEP, a ratio between inspiration time and expiration time, and breathing rate.

2. An apparatus as claimed in claim 1 wherein said calculating means comprises means for calculating said momentary compliance substantially continuously throughout a complete inspiratory phase.

3. An apparatus as claimed in claim 1 wherein said calculating means for calculating said momentary compliance as a ratio between momentarily measured flow and a time derivative of the measured pressure.

4. An apparatus as claimed in claim 1 wherein said adjustment means comprises means for increasing PEEP for a next inspiratory phase, following an inspiratory phase in which said momentary compliance is calculated, if the momentary compliance is less than said threshold value during an initial predetermined portion of said inspiratory phase.

5. An apparatus as claimed in claim 4 wherein said adjustment means comprises means for reducing PEEP for said next inspiratory phase if said momentary compliance exceeds a further threshold value during said initial predetermined portion of said inspiratory phase.

6. An apparatus as claimed in claim 1 wherein said adjustment means comprises means for changing said ratio between inspiration time and expiration time if said momentary compliance falls below said threshold after an end portion of said inspiratory phase for causing said momentary compliance in a next expiratory phase to exceed said threshold value during a corresponding portion of said inspiratory phase, while maintaining a predetermined minute volume of breathing gas to said respiratory system.

7. An apparatus as claimed in claim 1 wherein said adjustment means comprises means for changing the breathing rate if said momentary compliance falls below said threshold after an end portion of said inspiratory phase for causing said momentary compliance in a next expiratory phase to exceed said threshold value during a corresponding portion of said inspiratory phase, while maintaining a predetermined minute volume of breathing gas to said respiratory system.

8. An apparatus as claimed in claim 1 said adjustment means comprises means for changing said ratio between inspiration time and expiration time and the breathing rate if said momentary compliance falls below said threshold after an end portion of said inspiratory phase for causing said momentary compliance in a next expiratory phase to exceed said threshold value during a corresponding portion of said inspiratory phase, while maintaining a predetermined minute volume of breathing gas to said respiratory system.

9. A method for controlling a breathing apparatus comprising the steps of:

delivering a breathing gas to and removing expired breathing gas from, a respiratory system;

measuring a pressure and a flow of said breathing gas at least during delivery of said breathing gas;

calculating a momentary compliance of said respiratory system from respective measurements of said pressure and flow obtained at selected points in time during delivery of said breathing gas in an inspiratory phase;

comparing said momentary compliance to a threshold value; and if said momentary compliance is less than said threshold value, changing at least one parameter in a group of parameters consisting of pressure level, PEEP, a ratio between inspiration time and expiration time, and breathing rate.

10. A method as claimed in claim 9 comprising calculating said momentary compliance substantially continuously throughout a complete inspiratory phase.

11. A method as claimed in claim 9 comprising calculating said momentary compliance as a ratio between momentarily measured flow and a time derivative of the measured pressure.

12. A method as claimed in claim 9 wherein the step of changing at least one parameter comprises increasing PEEP for a next inspiratory phase, following an inspiratory phase in which said momentary compliance is calculated, if the momentary compliance is less than said threshold value during an initial predetermined portion of said inspiratory phase.

13. A method as claimed in claim 12 comprising reducing PEEP for said next inspiratory phase if said momentary compliance exceeds a further threshold value during said initial predetermined portion of said inspiratory phase.

14. A method as claimed in claim 9 wherein the step of changing at least one parameter comprises changing said ratio between inspiration time and expiration time if said momentary compliance falls below said threshold after an end portion of said inspiratory phase for causing said momentary compliance in a next expiratory phase to exceed said threshold value during a corresponding portion of said inspiratory phase, while maintaining a predetermined minute volume of breathing gas to said respiratory system.

15. A method as claimed in claim 9 wherein the step of changing at least one parameter comprises changing the breathing rate if said momentary compliance falls below said threshold after an end portion of said inspiratory phase for causing said momentary compliance in a next expiratory phase to exceed said threshold value during a corresponding portion of said inspiratory phase, while maintaining a predetermined minute volume of breathing gas to said respiratory system.

16. A method as claimed in claim 9 wherein the step of changing at least one parameter comprises changing said ratio between inspiration time and expiration time and the breathing rate if said momentary compliance falls below said threshold after an end portion of said inspiratory phase for causing said momentary compliance in a next expiratory phase to exceed said threshold value during a corresponding portion of said inspiratory phase, while maintaining a predetermined minute volume of breathing gas to said respiratory system.

\* \* \* \* \*